United States Patent [19]

Gabbai et al.

[11] Patent Number: 4,568,772

[45] Date of Patent: Feb. 4, 1986

[54] PROCESS FOR THE PREPARATION OF P-T-BUTYL-α-METHYLDIHYDROCIN-NAMALDEHYDE

[75] Inventors: Albert Gabbai, Meyrin; Karl-Fred De Polo, Onex, both of Switzerland

[73] Assignee: Givaudan Corporation, Clifton, N.J.

[21] Appl. No.: 532,233

[22] Filed: Sep. 14, 1983

[30] Foreign Application Priority Data

Sep. 21, 1982 [CH] Switzerland .......................... 5576/82
Aug. 10, 1983 [CH] Switzerland .......................... 4356/83

[51] Int. Cl.⁴ ............................................. C07C 45/00
[52] U.S. Cl. .................................... 568/436; 568/433; 544/178; 546/192; 548/578; 548/215; 564/383
[58] Field of Search ................................ 568/433, 436

[56] References Cited

U.S. PATENT DOCUMENTS 4,384,116  5/1983  Pfiffner .

FOREIGN PATENT DOCUMENTS 0045571  2/1982  European Pat. Off. .
2952719  7/1981  Fed. Rep. of Germany .

OTHER PUBLICATIONS

McOmie, Protective Groups in Organic Chemistry (1973) 323, 324, 337–340, 343, 344, 345 and 346.

Primary Examiner—Bernard Helfin
Attorney, Agent, or Firm—Robert F. Tavares

[57] ABSTRACT

This invention discloses a novel process for producing p-t-butyl-α-methyldihydrocinnamaldehyde which comprises converting the α-methyldihydrocinnamaldehyde to an enamine, oxazolidine or a Schiff's base, reacting said derivative with a tertiary butyl cation, and then removing the protective group.

8 Claims, No Drawings

PROCESS FOR THE PREPARATION OF P-T-BUTYL-ALPHA-METHYLDIHYDROCINNAMALDEHYDE

BACKGROUND OF THE INVENTION

1. Field of the Invention

Process for preparing p-t-butyl-α-methyldihydrocinnamaldelyde.

2. Prior Art

The compound p-t-butyl-α-methyldihydrocinnamaldehyde is one of the most important materials used in preparing fragrances. The usual method for preparing this compound is by the novel sequence of steps shown below.

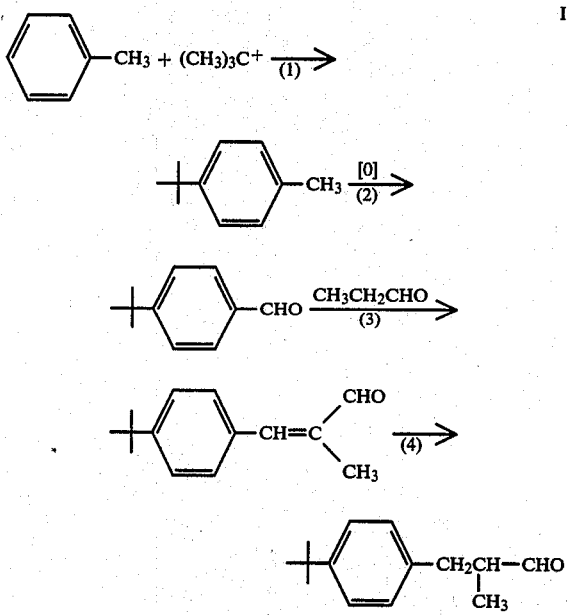

A process that could be commercially attractive in theory is one that would allow the use of benzaldehyde, an economical and readily available compound, as a starting material. Such a process would require introducing the tertiary butyl group in the presence of an aldehyde group. The practical reality is, however, that a tertiary butyl group cannot be introduced in the presence of an aldehyde group because the aldehyde group cannot survive the reaction conditions necessary to carry out the tertiary butylation.

Some attempts have been made to circumvent this problem by converting the aldehyde group to the more stable alcohol group. The tertiary butylation is then performed on the alcohol and the alcohol is oxidized back to the aldehyde. (See, for example, the German Offenlegungsschrift DE No. 2,952,719 published July 16, 1981 and European patent publication No. 45,571 published Feb. 10, 1982). The disadvantage of such processes is the necessity of converting the alcohol back to the aldehyde. Such reactions are difficult to perform efficiently and economically. At high conversions, oxidation of the aldehyde to the acid occurs and this results in lower yields of the desired product. Attempts to minimize acid formation by stopping the reaction at lower conversions results in a mixture of starting alcohol and aldehyde, a mixture which is not easily separated by a simple distillation. The fact that neither of the references cited above provide any information with respect to yields in the oxidation step is consistent with the known difficulty with such conversions.

There is no prior art which teaches the tertiary butylation of an aldehyde derivative which can be easily and efficiently converted back to the aldehyde after the tertiary butyl group has been added. The requirements for such a process are not easily met. The aldehyde derivative should be sufficiently labile to be easily converted back to the aldehyde, but sufficiently stable to survive the reaction conditions during the tertiary butylation.

SUMMARY OF THE INVENTION

It is the surprising and unexpected discovery of this invention that a α-methyldihydrocinnamaldehyde can be successfully converted to p-t-butyl-α-methyldihydrocinnamaldehyde by tertiary butylating the corresponding compound wherein the aldehyde group is protected as the enamine, oxazolidine or the Schiff's base. Surprisingly, these aldehyde derivatives survive the harsh reaction conditions necessary to effect a tertiary butylation sufficiently well to allow good yields of p-t-butyl-α-methyldihydrocinnamaldelyde to be prepared. The use of the Schiff's base for the tertiary butylation can be carried out in very high yield and it is especially preferred to use the Schiff's base in this process.

The process comprises tertiary butylating a compound of the formula

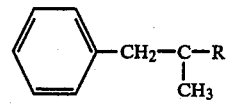

wherein:

R represents a formyl group protected as an enamine, oxazolidine or a Schiff's base, and the dotted line represents a bond when an enamine is used, and then removing the protecting group.

The compounds of formula II are novel and form a further object of the invention. They can be prepared from α-methylhydrocinnamaldehyde using known techniques for producing enamines, oxazolidines and Schiff's bases from aldehydes.

DESCRIPTION OF THE PREFERRED EMBODIMENTS

The enamine can be prepared via a procedure similar to those known in the art wherein an aldehyde is reacted with a suitable secondary amine such as a dialkyl amine (e.g. di-$C_{2-6}$-alkylamines such as diethylamine or dipropylamine) or a cyclic secondary amine (e.g. morpholine, piperidine or pyrrolidine). Morpholine and di-n-propylamine are the amines most commonly used and are preferred.

The amine can be used in equimolar amounts, but it is usually preferred to use a slight excess (10 to 20% excess). The reaction is usually carried out by heating at the reflux temperature in the presence of an inert solvent. The preferred inert solvents are those which form an azeotrope with the water formed in the reaction (e.g. cyclohexane, benzene, toluene or xylenes). It is also preferred to remove the water as formed, for example, by means of a Dean Starke apparatus. An acid catalyst is normally employed, for example, toluenesulphonic acid, camphorsulphonic acid, formic acid, benzoic acid or methanesulphonic acid. Formic acid is preferred.

The enamine formation can also be carried out using a Soxhlet extractor. The azeotrope (water-entraining solvent/water) is percolated in this Soxhlet extractor through a drying agent such as, for example, through a molecular sieve. The reaction temperature depends on the boiling point of the solvent/water azeotrope. It is preferred to choose a system that lies in the range of 80°–140° C.

The oxazolidine derivative of formula II can be prepared by reacting the aldehyde with monoethanolamine, diethanolamine or N-alkyl-N-ethanolamines, suitably in equimolar amounts but preferably with a 10–30% excess of the amine component. In other respects, the reaction is conveniently carried out in a manner similar to that described earlier for the enamine reaction.

Upon completion of the reaction, which is determined when no more water can be azeotropically removed from the reaction mixture, the solution of the enamines or oxazolidines in toluene, benzene or cyclohexane etc. can be washed with cold saturated sodium chloride solution. The solutions can then be dried over sodium sulphate and concentrated to yield the crude enamines or crude oxazolidines which can be used without further purification in the tertiary butylation reaction.

In order to form the Schiff's bases of formula II, the aldehyde is reacted with a primary amine in a manner similar to those known in the art for preparing Schiff's bases. Suitable amines are alkylamines (e.g. $C_{1-6}$-alkylamines such as methylamine, ethylamine, propylamine etc.) and alicyclic amines (e.g. cyclohexylamine, etc.) Methylamine and 2-butylamine are preferred. In other respects, the reaction is carried out as described earlier for the enamine formation and/or the oxazolidine formation.

The tert-butylation of a compound of formula II is carried out by reaction with a compound which yields the carbonium ion of the formula

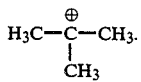

Preferred compounds which yield the carbonium ion of formula III are isobutylene, tert.butyl halides (e.g. tert.-butyl chloride) or tert.butyl alcohol.

The tert.butylation of a compound of formula II is carried out in the presence of a suitable amount of a Friedel-Crafts catalyst. Suitable catalysts are the known Fiedel-Crafts catalysts such as, for example, aluminium chloride, iron chloride, boron trifluoride or sulphuric acid. Sulphuric acid is especially preferred for the purpose of the present invention, there being used, for example, 2–10 mols, preferably 4–6 mols, of concentrated sulphuric acid per mol of the compound of formula II.

If desired, the reaction can be carried out in the presence of an inert organic solvent. Especially suitable inert organic solvents are alkanes such as hexane and cyclohexane and chlorinated hydrocarbons such as chloroform, ethylene dichloride and methylene chloride. Methylene chloride is preferred. The temperature at which the tert.butylation is carried out conveniently lies between about 0°–20° C., preferably between about 0°–10° C.

The reaction time can vary in a wide range. For example, it can range from 0.5 hour to several hours.

The cleavage of the protecting group from the p-tertiary butylated compound of formula II is conveniently carried out by simply diluting the reaction mixture with ice and water. The presence of a water-immiscible organic solvent such as methylene chloride, ethylene chloride, hexane, benzene, toluene, diisopropyl ether, diethyl ether and the like is convenient.

ILLUSTRATION OF THE PREFERRED EMBODIMENTS

Example 1

To a 4-necked round flask which is fitted with a stirrer, thermometer, dropping funnel and water separator there is added 74 g (0.5 mol) of α-methylhydrocinnamaldehyde and 150 ml of cyclohexane. Monoethanolamine (30.54 g, 0.5 mol) is added while stirring and cooling the mixture. After stirring the mixture for an additional 0.5 hour, 0.3 g of p-toluenesulphonic acid is added and the mixture is heated at reflux temperature until the theoretical amount of water has separated. Potassium carbonate (0.5 g) is now added and the mixture is stirred for 10 minutes. The mixture is thereupon filtered and the solvent removed on a rotary exaporator. There are obtained 94.4 g of the oxazolidine (theoretical yield 95.63 g).

The product is rectified over a 6 cm Vigreux column. The yield of pure product amounts to 56.5 g (59.1% of theory). B.p. 98° C. at 0.3 Torr; $n_D^{20} = 1.5270$. Since the oxazolidine decomposes partially in the distillative purification, the crude oxazolidine is preferably used for the next step. From the IR spectrum and the NMR spectrum it is evident that the reaction product is an equilibrium mixture (1:1) of the closed oxazolidine form and the open (Schiff's base) form:

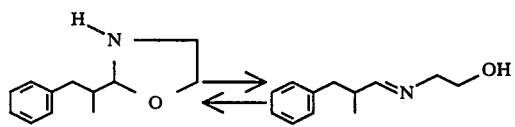

The tert.butylation is carried out in a 500 ml 4-necked sulphonation flask fitted with a thermometer, paddle stirrer, gas inlet tube and a rising tube which is immersed in saturated sodium chloride solution. The introduction of the isobutylene is carried out from a pressurized gas container which stands on a balance.

Concentrated sulphuric acid (62 g, 0.6 mol) is added to the reaction vessel. While cooling with a dry ice/isopropanol cooling mixture, a solution of 19.2 g of the oxazolidine in 80 ml of methylene chloride is allowed to drop in during 30 minutes at a temperature between 0° C. and 5° C. Isobutylene (7.4 g) is now introduced during 1 hour at a temperature of 18°–20° C. The mixture is subsequently stirred at 20° C. for a further 30 minutes. The mixture is then poured on to 550 g of ice. There initially forms a paste-like precipitate which passes into solution after standing for 2 hours. The mixture is transferred into a separating funnel and the aqueous phase is extracted twice with methylene chloride. The organic phase is washed neutral, dried over sodium sulphate and evaporated on a rotary evaporator. There are obtained 23.9 g of the crude aldehyde of formula I (theoretical yield 20.5 g). Fractional destillation gives 10.3 g of pure aldehyde of formula I of boiling point 100°–102° C./1 Torr; yield 50.2% of theory.

Example 2

To a 500 ml 4-necked flask which is fitted with a stirrer, water separator, dropping funnel and thermometer is added 74 g (0.5 mol) of α-methylhydrocinnamaldehyde and 150 ml of cyclohexane. Pyrrolidine (46 g, 0.65 mol) in which there is dissolved 0.1 g of p-toluenesulphonic acid is added slowly from the dropping funnel while vigorous stirring is maintained. The temperature of the mixture thereupon rises to 35° C. After the addition, which requires 30 minutes, the mixture is stirred at 35° C. for a further 30 minutes. A water separator is subsequently affixed and the reaction water is separated at reflux temperature. After 2.5 hours, 9.5 ml of water are separated in this manner. A small amount of potassium carbonate is added to the mixture and the resulting mixture is stirred and filtered. There is obtained 104 g of crude enamine in this manner. Fractional distillation gives 53 g of enamine of boiling point 124°–128° C./7 Torr; $n_D^{20} = 1.5434$; yield 52.7%.

The tert.butylation is carried out in a 250 ml 4-necked round flask which is fitted with a stirrer, thermometer, gas inlet tube and bubble tube for excess pressure.

Concentrated sulphuric acid (55 g) is added to the reaction vessel. While cooling the reaction mixture with an ice/sodium chloride cooling mixture, a solution of 20.5 g of the enamine prepared above in 80 ml of methylene chloride is added dropwise at a temperature of 5° C.–10° C. during 0.75 hour. The reaction mixture now becomes dark brown in color. The dropping funnel is now replaced by the gas inlet tube and 8.3 g of isobutylene are introduced during 1 hour at 19–20 C. After completion of the introduction, the mixture is stirred at room temperature for a further 1.5 hours. The mixture is thereupon poured while stirring into 500 ml of demineralized water and the mixture is stirred for 30 minutes. The organic phase is separated in a separating funnel and the aqueous phase is extracted with methylene chloride. The organic phases are washed neutral, dried and evaporated on a rotary evaporator. There is obtained 18.7 g of crude aldehyde of formula I. Distillation in a bulb-tube gives 8.6 g of pure aldehyde of formula I of boiling point 100°–102° C./1 Torr; the yield amounts to 42%.

Example 3

To a 250 ml 4-necked round flask which is fitted with a stirrer, thermometer and gas inlet tube is added 44.4 g (0.3 mol) of α-methylhydrocinnamaldehyde, 60.7 g (0.6 mol) of dipropylamine, 0.3 g of toluenesulphonic acid and 100 ml of cyclohexane. Some boiling stones are added and the mixture is heated at reflux temperature for 2.5 hours having a water separator to collect the water formed in the reaction. The reaction is followed by gas chromatography [column 2% OV 101 (methyl silicon of Applied Science Laboratories, Inc., P.O. Box 440, State College P.A.) on Chromosorb G. DMCS AW 80–100 mesh. Temperature 200° C., gas: helium; detector FID 250° C.]. 4.2 ml of water are separated (theoretical amount 5.4 ml). The mixture is concentrated on a rotary evaporator at 50° C./30 Torr. In this manner there are obtained 73.4 g of crude enamine (theoretical amount 69.4 g) which are subjected directly to the tert.butylation.

A small amount of the dipropyl enamine obtained is purified by fractional distillation. The pure product has a boiling point of 100° C./0.5 Torr; $n_D^{20} = 1.5030$.

The tert.butylation is carried out in a 350 ml 4-necked sulphonation flask which is fitted with a paddle stirrer, gas inlet tube and an excess pressure rising tube which is immersed in saturated sodium chloride solution. The isobutylene is introduced from a pressurized gas container standing on a balance.

Concentrated sulphuric acid (200 g) is weighed into the reaction vessel. The crude dipropyl enamine (73.4 g) prepared above in 80 ml of methylene chloride is slowly added dropwise thereto within 2.5 hours at −2° C. to 0° C. while cooling is maintained with an ice/sodium chloride cooling mixture. The mixture becomes red-brown in color. The dropping funnel is now replaced by the gas inlet tube and 22.4 g of isobutylene are introduced within 1.75 hours at a temperature between 17° C. and 19° C. After completion of the introduction, the mixture is stirred at room temperature for a further 1 hour. Ice (240 g) is then added while stirring continues. The organic phase is separated and the aqueous phase is extracted three times with methylene chloride. The combined organic phases are neutralized with about 20 ml of 50% potassium hydroxide solution. The solution is washed neutral and dried over sodium sulphate. After concentration on a rotary evaporator, there are obtained 63.1 g of crude aldehyde of formula I. By fractional distillation of the crude product there are obtained 27.8 g of pure aldehyde of formula I (yield 45.4%).

Example 4

To a stirred solution of 75.7 g of methylphenylpropanal in 125 ml of diisopropyl ether there is added slowly 40.2 g of 2-butylamine. The water formed in the reaction is separated using a water separator. After a reaction time of 5 hours, the solvent is evaporated and the crude imine (105 g) is subjected to short-path distillation, there being obtained 86 g of N-(2-methyl-3-phenylpropylidene)-2-butylamine in a purity of 96.4%; the yield amounts to 91.2%.

While stirring is maintained, 21.3 g of the imine are added within 1.5 hours to 62 g of 95% sulphuric acid. The mixture is cooled to 4° C. during the addition. Isobutylene (2.7 liters) is introduced into the stirred solution within 1.5 hours at 5° C.; thereupon 100 ml of methylene chloride are added thereto. The mixture is added, while stirring is maintained, to a mixture of 100 ml of methylene chloride and 522 g of 10% sodium hydroxide solution, the temperature being kept below 15° C. The organic phase is separated and washed with water until it has a slight alkaline reaction. After drying and evaporation of the solvent, there are obtained 29.1 g of the crude para-tert.butylated imine. Distillation over a 15 cm Widmer column yields 12.5 g of N-[p-tert-.butyl-(2-methyl-3-phenylpropylidene)]-2-butylamine in a purity of 91%; boiling point 106° C./0.6 Torr. 4.3 g of starting material are recovered. The aldehyde of formula I is obtained from the imine in a yield of 95% by the addition of 60 ml of 2N sulphuric acid at 5° C.

The imine (21 g) is added within 1 hour to 62 g of 95% sulphuric acid, the mixture being stirred continuously and the temperature being held below 8° C. Isobutylene (3.86 liters) is now introduced at 5° C. while stirring is maintained, the addition being carried out in 2.75 hours. Methylene chloride (40 ml) and water (40 ml) are thereupon added at 25° C. After working-up, evaporation of the solvent and short-path distillation, there is obtained 2-(p-tert.butylbenzyl) propanal in a yield of 85%.

The yields of the aldehyde of formula I obtained from related Schiff's bases are:

| Schiff's base | Yield |
|---|---|
| N—(2-Methyl-3-phenylpropylidene)methylamine | 82% |
| N—(2-Methyl-3-phenylpropylidene)cyclohexylamine | 75% |
| N—(2-Methyl-3-phenylpropylidene)aniline | 95% |
| N—(2-Methyl-3-phenylpropylidene)-1-butylamine | 70.7% |
| N—(2-Methyl-3-phenylpropylidene)-tert.butylamine | 64.5% |

Example 5

To a 250 ml round ground stoppered flask there is added 74.1 g of α-methylhydrocinnamaldehyde, 80 ml of cyclohexane and, while agitating, 65.4 g of morpholine, the temperature of the mixture rises to 57° C. A water separator is affixed and the reaction water is separated at reflux temperature. After a reaction period of 3 hours, 9.2 ml of water are separated in this manner. Analysis by gas chromatography shows that about 5% of unchanged aldehyde starting material are still present. By percolating the boiling water-entraining agent (solvent) in the Soxhlet extractor over 5 g of 3A molecular sieve the remaining starting material has also reacted completely.

After evaporation of the water-entraining agent (cyclohexane) on a rotary evaporator, there are obtained 117.8 g of crude enamine. This is subjected to a short-path distillation in a bulb-tube, there being obtained 101.7 g of crude enamine of boiling point 125° C./0.06 Torr; $n_D^{20}=1.5362$; yield 92.8%.

Concentrated sulphuric acid (155 g) is weighed into a 500 ml sulphonation flask which is fitted with a stirrer, thermometer and dropping funnel. The morpholine enamine (54.3 g) is introduced dropwise while stirring and cooling with an ice/sodium chloride cooling mixture to a temperature below 5° C. The dropping funnel is subsequently replaced by a gas inlet tube which is immersed in the mixture. Moreover, the sulphonation flask is connected to an outlet tube which is immersed in saturated sodium chloride solution. Isobutylene (23.8 g) is subsequently introduced while stirring at a temperature below 10° C. during 80 minutes from a pressurized gas container standing on a balance. The mixture is stirred for 1 hour at 10° C. and subsequently poured into a mixture of 100 ml of ether and 1 kg of ice.

The organic phase is separated and the aqueous phase is extracted twice with ether. The combined organic phases are separated and washed neutral. After drying over sodium sulphate and evaporation of the solvent, there are obtained 47.5 g of crude product. This is subjected to short-path distillation in a bulb-tube. 40.6 g of an aldehyde mixture are obtained. Analysis by gas chromatography indicates that the mixture consists of 60.3% of the aldehyde of formula I and 37% of α-methylhydrocinnamaldehyde. Yield: 47.8% of the aldehyde of formula I. A further purification can be carried out by column distillation.

We claim:

1. A process for the manufacture of p-t-butyl-α-methyldihydrocinnamaldehyde from α-methyldihydrocinnamaldehyde which comprises:
   (a) converting the α-methyldihydrocinnamaldehyde to an enamine, oxazolidine or Schiff's base,
   (b) reacting said enamine, oxazolidine or Schiff's base with a tertiary butyl cation derived from isobutylene, a t-butyl halide or t-butanol in concentrated sulfuric acid at a temperature of between 0° C. and 20° C., and
   (c) removing the protecting group by pouring the completed reaction mixture onto ice and water.

2. A process according to claim 1 which comprises:
   (a) reacting α-methyldihydrocinnamaldehyde with a secondary amine chosen from the group consisting of:
      (i) dialkylamines having from two to six carbon atoms and
      (ii) morpholine, piperidine and pyrrolidine to form the corresponding enamine, and
   (b) reacting said enamine, with a compound selected from the group consisting of isobutylene, t-butanol and a t-butyl halide in the presence of a Friedel-Crafts catalyst.

3. A process according to claim 2 wherein the enamine is reacted with isobutylene.

4. A process according to claim 1 which comprises:
   (a) reacting α-methyldihydrocinnamaldehyde with a compound selected from the group consisting of monoethanolamine, diethanolamine, or an N-alkyl-N-ethanolamine to form the corresponding oxazolidine, and
   (b) reacting said oxazolidine with a compound selected from the group consisting of isobutylene, t-butanol and a t-butyl halide, and in the presence of a Friedel-Crafts catalyst.

5. A process according to claim 4 wherein the oxazolidine is reacted with isobutylene.

6. A process according to claim 1 which comprises:
   (a) reacting α-methyldihydrocinnamaldehyde with a primary amine chosen from the group consisting of primary amines of from one to six carbon atoms to form the corresponding Schiff's base, and
   (b) reacting said Schiff's base with a compound selected from the group consisting of isobutylene, t-butanol and a t-butyl halide in the presence of a Friedel-Crafts catalyst.

7. A process according to claim 6 wherein the Schiff's base is reacted with isobutylene.

8. The process of claim 7 wherein the amine used to make the Schiff's base is chosen from the group consisting of methylamine, ethylamine, propylamine, butylamine, cyclohexylamine and aniline.

* * * * *

UNITED STATES PATENT AND TRADEMARK OFFICE
CERTIFICATE OF CORRECTION

PATENT NO. : 4,568,772
DATED : Feb. 4, 1986
INVENTOR(S) : A. Gabbai, K. DePolo

It is certified that error appears in the above-identified patent and that said Letters Patent is hereby corrected as shown below:

In the specification at column 2, lines 32-37 correct

" 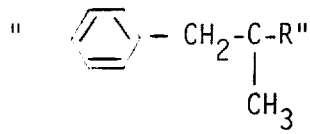 "

to read

-- 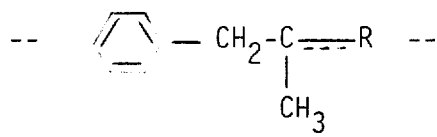 --

Signed and Sealed this

Seventeenth Day of July, 1990

Attest:

HARRY F. MANBECK, JR.

*Attesting Officer*  *Commissioner of Patents and Trademarks*